United States Patent [19]

Halstead

[11] Patent Number: 6,165,797

[45] Date of Patent: Dec. 26, 2000

[54] METHODS FOR TESTING OXIDATIVE STRESS

[75] Inventor: Bruce W. Halstead, Grand Terrace, Calif.

[73] Assignee: Bio-Defense Nutritionals, Inc., Grand Terrace, Calif.

[21] Appl. No.: 09/253,223

[22] Filed: Feb. 19, 1999

[51] Int. Cl.[7] .......................... G01N 21/78; G01N 33/493
[52] U.S. Cl. .......................... 436/128; 436/166; 436/130; 436/808
[58] Field of Search ..................... 436/128, 130, 436/166, 808; 422/61

[56] References Cited

U.S. PATENT DOCUMENTS 4,753,891   6/1988   Thompson et al. ..................... 436/130
5,950,634   9/1999   Ochi et al. ............................... 128/898
5,985,665   11/1999  Crawford et al. ....................... 435/404

*Primary Examiner*—Lyle A. Alexander
*Attorney, Agent, or Firm*—Fish & Associates, LLP

[57] ABSTRACT

Urine is tested for presence of malondialdehyde by mixing it with a reagent consisting of about 90–110 parts 20% acetic acid, about 13.5–16.5 parts Ingredient A, and about 4.5–5.5 parts Ingredient B, wherein Ingredient A is comprised of sodium metabisulfite, phosphoric acid and deionized water in the proportions of about 18–22 grams sodium metabisulfite, 9–11 ml of concentrated phosphoric acid, and about 450–550 ml deionized water, and Ingredient B is comprised of basic fuchsin and Ingredient A in the proportion of about 0.45–0.55 grams basic fuchsin to about 90–110 ml Ingredient A. A color change is observed when malondialdehyde is present in the urine in a concentration greater than about 2 ppm.

6 Claims, No Drawings

METHODS FOR TESTING OXIDATIVE STRESS

FIELD OF THE INVENTION

The present invention relates generally to the field of material and methods used for the detection of malondialdehyde in urine.

BACKGROUND

It is by now common knowledge that stress in mammalian subjects develops directly or indirectly into a display of oxygenated activities that quickly changes the usual reduced state of the body. This hyperoxygenated state—with resulting hydroxides, peroxides and related free radical states— can cause great physical imbalance and actual physical damage that can change pathological states, which in turn develop into atherosclerotic plaques. Such plaques can result in the deposition of high lipid levels particularly in a blockage of arteries that can cause a cessation of blood flow to the heart with a resulting heart attack. This is one of but many human disease states that are caused by free radical attack from the hyperoxygenated state caused by stress. What is not appreciated what markers can be utilized to measure oxidative stress.

Malondialdehyde is a component of normal urine. Its presence can be determined quantitatively using equipment such as spectrophotometers, fluorometers, high performance liquid chromatographs and gas chromatograph mass spectrometers. In another method applicable to aldehydes in general, (disclosed at page 395 in "Qualitative Analysis by Spot Tests", Third Edition, authored by F. Feigl and published by Elsevier Publishing Company, Inc.), a drop of sample solution which may contain aldehyde is mixed with 2 ml of 72 percent sulfuric acid in a test tube. A small amount of solid chromatropic acid (1,8-dihydrooxynapthlanene-3,6 disulfate) is added and the test tube is heated in a 60?C water bath for about ten minutes. A bright violet color appears in the presence of aldehyde; sensitivity of the test is reportedly about 3 ppm of aldehyde.

In yet another method generally applicable to aldehydes, described at pages 339–340 of the Feigl publication, a drop of aqueous (or alcoholic) solution suspected of containing an aldehyde is treated on a spot plate with a drop of sulfurous acid and a drop of fuchsin/sulfuric acid and allowed to stand. A red to blue color appears within about two to thirty minutes, according to the amount of aldehyde present in the test solution being tested. Such test is reportedly sensitive to about one microgram of formaldehyde in the drop of solution being tested. The problem with such a test, and other known aldehyde tests, is that the tests are not quickly and easily performed. The first above-described test, for example, requires heating of a test tube of solution in a constant temperature water bath for ten minutes.

Despite the prior existence of these tests, it has never been appreciated that such tests can be applied to malondialdehyde in urine to detect oxidative stress Thus, there is still a need to provide methods and apparatus for detecting oxidative stress in subjects.

SUMMARY OF THE INVENTION

The present invention provides methods and apparatus for detecting malondialdehyde in urine, utilizing a reagent comprising about 90–110 parts 20% acetic acid, about 13.5–16.5 parts Ingredient A, and about 4.5–5.5 parts Ingredient B, wherein Ingredient A is comprised of sodium metabisulfite, phosphoric acid and deionized water in the proportions of about 18–22 grams sodium metabisulfite, 9–11 ml of concentrated phosphoric acid, and about 450–550 ml deionized water, and Ingredient B is comprised of basic fuchsin and Ingredient A in the proportion of about 0.45–0.55 grams basic fuchsin to about 90–110 ml Ingredient A.

In preferred embodiments the proportion of acetic acid, Ingredient A and Ingredient B are about 100 parts 20% acetic acid, about 15 parts Ingredient A, and about 5 parts Ingredient B. In more preferred embodiments, the proportions for Ingredient A are about 20 grams sodium metabisulfite, about 10 ml of phosphoric acid, and about 500 ml deionized water. In still more preferred embodiments the proportions for Ingredient B are about 0.5 grams basic fuchsin to about 100 ml Ingredient A.

DESCRIPTION OF THE PREFERRED EMBODIMENT

It has been discovered that the oxidative stress state of a person can be measured from the release into the urine of malondialdehyde, and that a fuchsin based colorimetric test can measure the released malondialdehyde in a rapid, easily performed home test kit form by using the reagent described below with a small quantity of urine. The resulting color formed is compared to a calibrated test strip to assess the level of stress from a negative value through levels of +1 to +3, with the main goal of demonstrating a measurable stress which can be treated with the common antioxidant vitamins A, C and E, and antioxidant minerals. Retesting after a suitable period of time can assess the adequacy of the antioxidant therapy.

According to the present invention, a testing solution or reagent for testing for the presence of aldehyde in an aqueous solution comprises a solution of acetic acid, preferably about 20% acetic acid, and two additional ingredients designated herein as "Ingredient A" and "Ingredient B". Ingredient A consists essentially of sodium metabisulfite, phosphoric acid, and deionized water. The preferred proportions of the elements of ingredient A are about 18–22 grams sodium metabisulfite, 9–11 ml of concentrated phosphoric acid, and about 450–550 ml deionized water. Most preferably, the proportions are 20 grams sodium metabisulfite, 10 ml phosphoric acid, and about 500 ml deionized water. Ingredient B consists essentially of a mixture of basic fuchsin (certified grade) and Ingredient A in the preferred proportions of about 0.45–0.55 grams basic fuchsin in about 90–10 ml of Ingredient A. Most preferably, the proportions are about 0.50 grams of basic fuchsin in about 100 ml of Ingredient A.

The components of the reagent are mixed in the proportion of about 90 to 110 parts of 20% acetic acid, 13.5–16.5 parts Ingredient A, and about 4.5–5.5 parts Ingredient B. An alternative method of making the reagent is as follows. First, dissolve 4 grams of sodium metabisulfite in 80 ml of deionized water. Then, add 2 ml of concentrated phosphoric acid, and dilute the mixture with a quantity of deionized water sufficient to make 100 ml of dilute mixture. Then add 0.5 gram of basic fuchsin, and about 10 grams of bone charcoal to decolorize the mixture. Remove the charcoal by centrifuging and filtering the mixture. Then, to 100 ml of the decolorized solution, add 100 ml of 20%–40% glacial acetic acid, and finally, add 100 ml of deionized water. The active components are present in the reagent made this way in about the same proportion as in the method previously described.

The testing solution described above is preferably stored in individual, sealed test-size ampoules or vials of conventional medical solution type. When packaged in such a manner and stored in a cool, dry place, the sealed bottles or vials have an expected shelf storage life of at least 12 months. Assurance of active testing solution may be achieved, as described below, by positive aldehyde test procedures.

A test for the presence of malondialdehyde in an aqueous solution is then made by mixing about 1 ml of test solution (containing traces of aldehyde) into about 0.2–0.6 ml of testing solution formulated as above. If the mixture of the test sample and testing solution remains colorless after a waiting period of about 2–5 minutes, the test is negative and the test sample therefore contains less than about 2 ppm aldehyde. Any color change of the mixture indicates presence of aldehyde in the test solution in a concentration greater than about 2 ppm. A positive malondialdehyde test is preferably by quality control techniques made before testing the test samples to assure that the testing solution is properly formulated or that, for example, the reagent bottles have not been replaced with other bottles containing non-testing solutions.

The positive malondialdehyde test is preferably performed by injecting 1 ml of available "Positive Aldehyde Test Solution (Standard)" into a bottle containing about 0.2–0.6 ml of the test solution. In approximately 2–5 minutes, the solution in the bottle should develop a pinkish-purple color provided the bottle contains properly formulated aldehyde testing solution. Otherwise, the bottle of "testing solution" from which the test bottle was selected should be discarded. The above-described positive test for aldehyde is sensitive to 10 ppm or more of aldehyde. For a 5 ppm, a positive test for aldehyde, 0.5 ml of deionized water is used. A color less intense than that of the 10 ppm aldehyde test is obtained for the 5 ppm aldehyde test.

Basic fuchsin is a purple powder which reacts with aldehydes in the skin, urine or blood plasma. With low or no aldehydes present, you get no color development. With moderate or high levels of aldehydes you get color gradations roughly dependent on the level of aldehydes present. The amino group of the fuchsin couples with the aldehyde to produce the pink to purple color approximately dependent on the amount of aldehyde present in the blood or urine. A 40% glacial acetic acid solution gives maximum color development for the fuchsin reaction. Sodium metabisullite ties up free oxygen so that only the aldehydes react with the fuchsin group. Basic fuchsin changes color in an acidic solution, relative to the amount of aldehyde present in the urine samples. The color developed depends on the pH, which is controlled by the amount of acid present. Metabisulfite is used to stop the interference of oxygen from air. Establishing a nitrogen blanket over the reagent mixture gives greater shelf life of the reagent to stop any oxygen reaction with the reagent. The phosphoric acid stabilizes the pH in a rough adjustment and the acetic acid gives the fine acid pH stabilization. Malondialdehyde (MDA) and other related aldehydes are released from the breakdown of long chain polunsaturated fatty acids by free radical attack. High levels of MDA and related aldehydes are found in a variety of diseases and abnormal metabolism states such as coronary artery disease, diabetes, and Parkinson disease.

Since the invention is subject to modifications and variations, it is intended that the foregoing description and the accompanying drawings shall be interpreted as only illustrative of the invention defined by the following claims.

I claim:

1. A method of using a test kit for detecting malondialdehyde in urine; wherein the test hit comprises a reagent comprising about 90–110 parts 20% acetic acid, about 13.5–16.5 parts Ingredient A, and about 4.5–5.5 parts Ingredient B, wherein Ingredient A is comprised of sodium metabisulfite, phosphoric acid and deionized water in the proportions of about 18–22 grams sodium metabisulfite, 9–11 ml of concentrated phosphoric acid, and about 450–550 ml deionized water, and Ingredient B is comprised of basic fuchsin and Ingredient A in the proportion of about 0.45–0.55 grams basic fuchsin to about 90–110 ml Ingredient A; combining the reagent with the urine sample to produce a colored product; and comparing the color of the product with a reference chart to determine the amount of malondialdehyde in the sample.

2. The method of claim 1, wherein the proportion of acetic acid, Ingredient A and Ingredient B are about 100 parts 20% acetic acid, about 15 parts Ingredient A, and about 5 parts Ingredient B.

3. The method of claim 1, wherein the proportions for Ingredient A are about 20 grams sodium metabisulfite, about 10 ml of phosphoric acid, and about 500 ml deionized water.

4. The method of claim 1, wherein the proportions for Ingredient B are about 0.5 grams basic fuchsin to about 100 ml Ingredient A.

5. The method of claim 1, wherein the step of combining the reagent with the urine sample includes allowing the product to stand at least about 2 minutes prior to comparing the color.

6. The method of claim 1, further comprising a step of sealing the testing reagent in a ampule and then injecting the test specimen into said ampule with a plastic bulb.

* * * * *